United States Patent [19]

Salesky

[11] Patent Number: 4,526,179
[45] Date of Patent: Jul. 2, 1985

[54] DIGITAL APICAL FORAMEN LOCATING APPARATUS

[75] Inventor: Leonard Salesky, 41 Polk St., Riverside, N.J. 08075

[73] Assignees: Leonard Salesky; Phyllis S. Farber, both of Riverside, N.J.

[21] Appl. No.: 461,914

[22] Filed: Jan. 28, 1983

[51] Int. Cl.³ .......................... A61C 19/04; A61B 5/05
[52] U.S. Cl. ....................................... 128/776; 433/27; 128/777
[58] Field of Search ................... 128/776, 777, 734; 433/27, 28, 229, 32; 33/174 D

[56] References Cited

U.S. PATENT DOCUMENTS

| | | | |
|---|---|---|---|
| 3,058,225 | 10/1962 | Ward | 128/776 |
| 3,993,044 | 11/1976 | McGuffin | 433/27 |
| 4,083,366 | 4/1978 | Gombrich et al. | 128/706 |
| 4,192,321 | 3/1980 | Korber et al. | 128/776 |
| 4,193,408 | 3/1980 | Fujino | 128/776 |
| 4,273,531 | 6/1981 | Hasegawa | 433/27 |
| 4,353,693 | 10/1982 | Déry et al. | 128/776 |

Primary Examiner—Lee S. Cohen
Assistant Examiner—Steven Falk
Attorney, Agent, or Firm—Thomas A. Lennox

[57] ABSTRACT

A numeric readout device is provided to display the distance of an instrument in a tooth from the peridontal membrane surrounding the tooth, including a pair of oscillator circuits with a numerical relationship determinator reading a distance measurement depended upon the impedance between the instrument and the gingival sulcus.

11 Claims, 3 Drawing Figures

DIGITAL APICAL FORAMEN LOCATING APPARATUS

BACKGROUND OF THE INVENTION

This invention relates to instrumentation to measure and numerically display the distance from a point position of a conductor within a tooth to the peridontal membrane surrounding the tooth. More particularly, it relates to instrumentation to measure the actual length of a root canal in a tooth and the position of an electrically conductive probe in the canal with respect to the apical foramen of the root canal and provide the numerical display of the distance.

This invention specifically relates to the instrumentation to aid in the treatment of and cleaning out the root or roots of a tooth for which root canal nerve removal is necessary to prevent the loss of the tooth. Throughout this specification the term "instrument" includes a variety of devices used to insert into the tooth for direct treatment or as indirect aids in providing treatment, specifically including reamers, files and like instruments used to clean out the pulp of a tooth, pins, posts and like anchors fixed into the tooth, electrically conductive canal filing such as silver points, conductive plastic material and the like, syringe needles used to inject a filling into the root canal or another cavity, and like instruments. In the root canal cleaning process, it is necessary to use cleaning instruments to remove essentially all of the vital and non-vital pulp tissue, debris, and other contents of canal out of the root canal of the tooth all the way to, or at least close to, the apical foramen, referred to throughout as the apex. The position of an instrument in the pulp is extremely important as over-penetration through the apex through the peridontal membrane and into the tissue below the tooth is clearly over instrumentation. Pushing the instrument too far creates the risk of pressing contaminated contents of the canal into the periapical tissue and may result in excess root filling to an incorrect distance. Going too far in root canal preparation leads to patient suffering and undesirable side effects.

It is well recognized that the use of radiographs for the determination of the apex location is inadequate at best, leading to substantial errors and over instrumentation. In a *Journal of Dentistry Research* article, published April 1962, Vol. 41, No. 2, titled "Measurement of Root Canal Length, Imao Sanada discussed a new method using an apparatus " . . . to measure electrical resistance . . . " between an " . . . anode . . . inserted into the canal . . . " and a " . . . cathode . . . placed on the buccal mucous membrane, . . . ." The circuit was adjusted before each reading to a set current to calibrate the device. Dial readings on this type of instrument are not quantitatively distance readings. Subsequently, devices have been offered utilizing sounds to signal penetration position. Noboru Inoue described in his U.S. Pat. No. 3,660,901 an *INSTRUMENT OF PROBING THE LENGTH OF A ROOT CANAL OF THE TOOTH*, that issued May 9, 1972. Later a second sound was added to provide a reference standard against which the probe sound is compared. These devices are described in various papers and publications including *A Clinical Evaluation of a Electronic Root Canal Measurement* (Sono Explorer) by Captain Larry J. O'Neil, CPT DC, USA, presented to the Dental Educational Committee, Fort Sill, Okla., Mar. 25, 1973, and reprinted in *Oral Surgery, Oral Med., Oral Pathology*, Volume 38-number 3, pages 469–473, September 1974; an article entitled *Clinical Evaluation of the Sono Explorer* by John J. Plant, D.D.S., et al, published in *The Journal of Endodontics*, Volume 2, number 7, July 1976, pages 215 and 216; and an article entitled *Determination of the Accuracy of the Sono-Explorer for Establishing Endodontic Measurement Control* by Leigh R. Busch, published in *The Journal of Endodontics*, Volume 2, number 10, October 1976, pages 295–297, all the above incorporated herein by reference. A device is described in a publication dated Apr. 27, 1979, entitled *Determining Root Canal Length* by Noboru Inoue, et al, describing the Sono-Explorer Mark II including a description of circuit layout and operation incorporated herein by reference. Difficulties with the operation of these and similar devices have resulted in the problem of audible recognition of the sound changes necessary to be recognized as the instrument approaches the apex. Some of these devices have utilized the principle beat as frequency as the two wave forms approach a null condition to produce a clear tone as the probe approaches the apex. The device may be modified to produce a short period of silence when the sound waves cancel each other before the sound begins again as the probe is pushed past the apex. If the probe is moved too quickly, it will pass through the silence period and the beat on the opposite side of the apex sounds identical to that of the beat it had during the approach. Dials reading current passage do not measure distance. Therefore, over-instrumentation can occur. Lights have been employed to signal the approach of the probe to the apical foramen including U.S. Pat. No. 4,353,693 to Tibor Dery et al, issued Oct. 12, 1982, incorporated herein by reference. These lights provide an optical warning, but do not yield a measurement of the distance involved. Most endodontists prefer to approach the apex but not pierce it. Doctors differ as to best distance of penetration. While many doctors prefer to reach the apex, many doctors prefer only to reach the apical constriction in the canal generally located approximately 0.5 millimeters short of the apex. The prior art devices do not allow for this type of approach and do not provide for easy stopping short of the apex in this manner.

The present invention satisfies these needs and attains the objects provided herein as well as those that will be clear from the description of the invention.

SUMMARY OF THE INVENTION

An object of this invention is to provide a digital readout of the distance between the end of a probe inserted into the root canal of a tooth and the apex of that canal, in the region near the apex of the canal.

An additional object of this invention is to provide a reading digital readout of the apical end of an instrument to read the position with respect to the peridontal membrane surrounding the tooth.

It is a particular object of this invention to provide a device to provide numeric readout upon demand indicating the penetration of the tooth by an instrument into the root canal without requiring continuous attachment of a wire to the instrument, thus allowing the tactile sense of the doctor not to be interfered with while using the instrument.

A further object of this invention is to provide an apparatus providing a numeric readout of the distance between the end of a mechanical reaming device and the apical foramen of the root canal, in the region near the apical foramen.

An additional object of this invention is to provide an apparatus capable of a numeric readout of the distance of penetration of an instrument in the root canal to the apical foramen while a substantial portion of the pulp remains in the canal.

A further object of this invention is to provide a numeric reading apparatus for measuring the penetration into a tooth without requiring constant resetting before use.

A further object of this invention is to provide an apparatus capable of numeric readout of the penetration of an instrument into the tooth with the capability of calibration to compensate for individual resistance of the patient to yield higher sensitivity of the measurement.

A further object of this invention is to provide an apparatus with a numeric readout of penetration into the tooth and in addition providing a separate signal indicating the position either above or below the apical foramen.

An additional object of this invention is to provide an apparatus with a numeric readout of the position of an instrument in the root canal with the capability of choosing whether the operator wishes to (a) preset the apparatus so that a zero reading will be a chosen distance above the apical foramen or (b) leave the instrument to read zero at the apical foramen and stop short a chosen distance above the level, or (c) continue penetration to a depth essentially exactly to the apical foramen to a zero readout.

The invention is an apparatus to determine the position of an instrument inserted into the tooth with respect to a point on the peridontal membrane surrounding the tooth. A particular use for this invention is to determine the distance of the apical end of the instrument inserted into the root canal of the tooth to the apex of the root canal and to display that distance numerically on a continuous readout. The apparatus includes a first electrical contact device capable of electrically connecting to an electrical return to the patient. In general usage, this electrical return to the patient is preferably a contact to the mucous membrane in the area of the mouth near the tooth to be treated. A second electrical contact device is included capable of electrically connecting to an instrument for penetration into the tooth. A first oscillator device to continuously generate an oscillating wave signal is electrically connected across the first and second contact devices wherein the frequency of the wave signal is dependent upon the conductives between the first and second contact devices. A second oscillator device to continuously generate an oscillating wave signal as a reference signal set to a constant frequency. Preferably, this constant frequency is one set through experience by the doctor or may be set for each patient as dependent upon the impedance between the first contact device and a position on the gum line next to the tooth to be treated, that is essentially the peridontal membrane.

An arithmetic frequency measuring and transmitting device to perform an arithmetic operation and determine an arithmetic relationship between the signal of the first oscillator means and the signal from the second oscillator means and transmit that arithmetic relationship is provided. A counter means to determine the value of the arithmetic relationship and transmit a coded signal of the relationship value is connected. A decoder device receives the coded signal and converts it to another signal to light the appropriate sections of a display. A register device holds the coded signal and conveys a second coded signal upon receipt of the update interrupt signal. An update device to cause removal of the information in the register device after a duration of a pre-set period of time wherein the time is chosen as directly proportional to a unit of distance of the instrument travel. A reset device is connected to cause the counter device to resume counting again immediately after the interruption of the update device. A numerical display device is provided to display the arithmetic relationship. Although not provided above, it is clear that an energy source and electrical connection between these elements of the apparatus is provided. There are a number of configurations of the elements available to achieve many of the objects above. While certain configurations are preferred, rearrangement of these elements into a variety of circuits is clearly available to achieve many of the objects of this invention. Preferred embodiments follow as to certain configurations of these elements.

DESCRIPTION OF PREFERRED EMBODIMENTS

Figure 1:
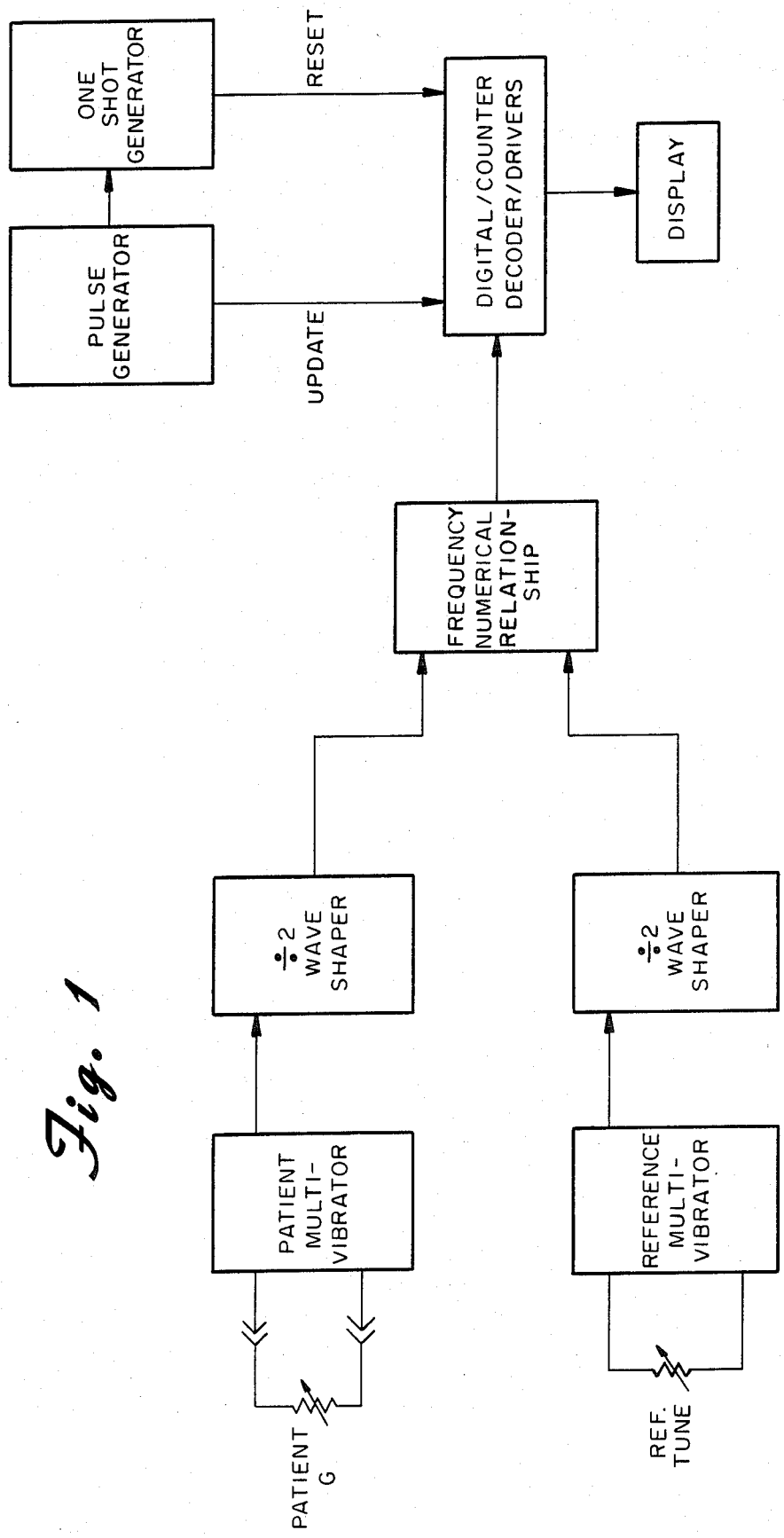
FIG. 1 is a block scheme showing the operation of an apparatus of the present invention.

The overall description of an apparatus of this invention is illustrated in FIG. 1. Two connecting devices contacts, the first capable of attachment to a lip clip or like electrical contact to the oral mucous membrane, and a second connecting device capable of attachment to an instrument, such as a dental appliance, inserted into and providing a contact in the tooth are provided. A patient oscillator device generates a wave form frequency dependent upon the impedance between the two contacts. A preferred embodiment includes a "divide by two" circuit device to act as a wave shaper as the frequency is halved. To act as a comparitor, a reference oscillator balanced to the patient oscillator is used to calibrate the instrument. This comparitor generates a frequency chosen by the operator through experience or at a value determined as the instrument contact is placed in the gingival sulcus, essentially to the peridontal membrane, preferably of the tooth to be treated. This frequency value turns out to be nearly a constant for most individuals so that it is not always necessary to adjust it from patient to patient. Again, a preferred embodiment includes the "divide by two" circuit wave shaper device receiving the comparitor frequency to balance the patient oscillator source. Both waves are received by the frequency numerical relationship determinator device which may compare the two frequencies by any number of numerical functions. These may include the preferred subtractive determination between the two frequencies to obtain the difference between the two, or with different circuitry, the sum, product, dividend, or some combination thereof, such as a log function. The arithmetic function is transmitted along the circuit from the determinator device. This arithmetic result in the form of pulses per unit time is received by the digital/counter/decoder/drivers circuit, which receives the arithmetic function, counts the pulses, and transmits them to the digital display upon command. A pulse generating device provides that command to update the display readout. This time for update is adjusted to be proportional to the actual distance to be measured in the patient's tooth. The one shot pulse generator gives a command to the digital counter to reset and begin counting again for the pre-set period of time controlled by the update pulse.

Figure 2:
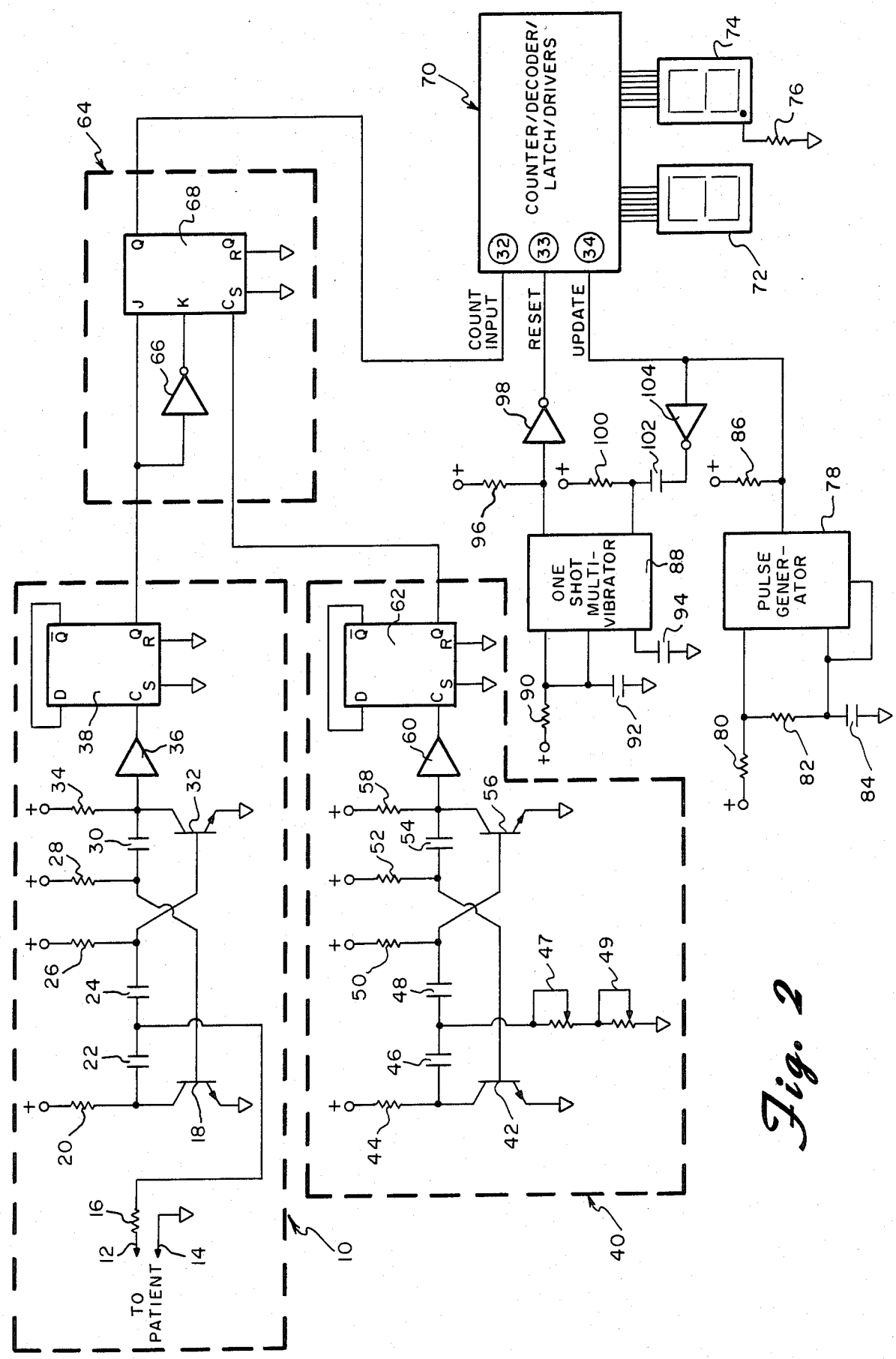
FIG. 2 is a schematic diagram illustrating the arrangement of the circuitry of an apparatus according to the scheme of FIG. 1.

A schematic diagram illustrating an embodiment of a circuit of the device illustrated in FIG. 1 is provided in FIG. 2. The patient oscillator circuit 10 utilizes the electrical contact 12 to the mucous member contact device with resistor 16, capacitor 22, capacitor 24 and resistor 26 being the time constant circuit for standard 2N4124 transistor 32, and resistor 28 and capacitor 30 being the time constant circuit for 2N4124 transistor 18. Resistor 20 is a collective load resistor for the circuit to buffer wave shaper 36 which triggers D flip flop "divide by two" standard circuit 38. The reference oscillator circuit 40 is essentially identical to that of circuit 10 with the added trimmer 47 to calibrate the circuit in series with tuning potentiometer 49 to ground connected between capacitors 46 and 48. A 2N4124 transistor 42 is connected through the time constant circuit of resistor 52 and capacitor 54 and resistor 44, capacitor 46, capacitor 48, and resistor 58 as the time constant circuit for 2N4124 transistor 56, vibration signal passing through to buffer wave shaper 60 connected and to a D flip flop "divide by two" circuit 62, identical to circuit 38.

The two pulse trains are received by subtraction circuit 64 utilizing a portion of a standard JK flip flop circuit chip 68 and inverter 66. The terminal designations shown on circuit 68 are provided from the literature on this standard circuit. The difference result signal is connected through the count input line to the counter/decoder/latch/drivers circuit 70, a circuit chip designated ICM7225 supplied by Intersil, Inc., 10710 North Tanton Avenue, Cupertino, Calif. 95014, in their Bulletin (1980) 12-79-00B, which in turn drives 7 segment LED display 72, reading 0 to 9 millimeters, and seven segment LED display 74, reading 0 to 0.9 millimeters, with ground resistor 76 connected to activate the decimal point. The update circuit includes a standard 555 timing chip 78 connected as a pulse generator to resistor 80 resistor 82, and resistor 84 to form a time constant circuit to provide a proper scale factor for the instrument. The pulse generator to circuit 70 is connected with pull up resistor 86. The reset circuit is centered around standard 555 circuit chip operating as a "one-shot" circuit 88 connected to timing constant circuit of capacitor 92 and resistor 90 and triggered from update pulse through inverter 104 and by coupling network of resistor 100 and capacitor 102. Bypass capacitor 94 is attached to the chip 88 to ground. The output of one-shot 88 is fed to reset connection of circuit 70 through inverter 98 with pull up resistor 96.

Figure 3:
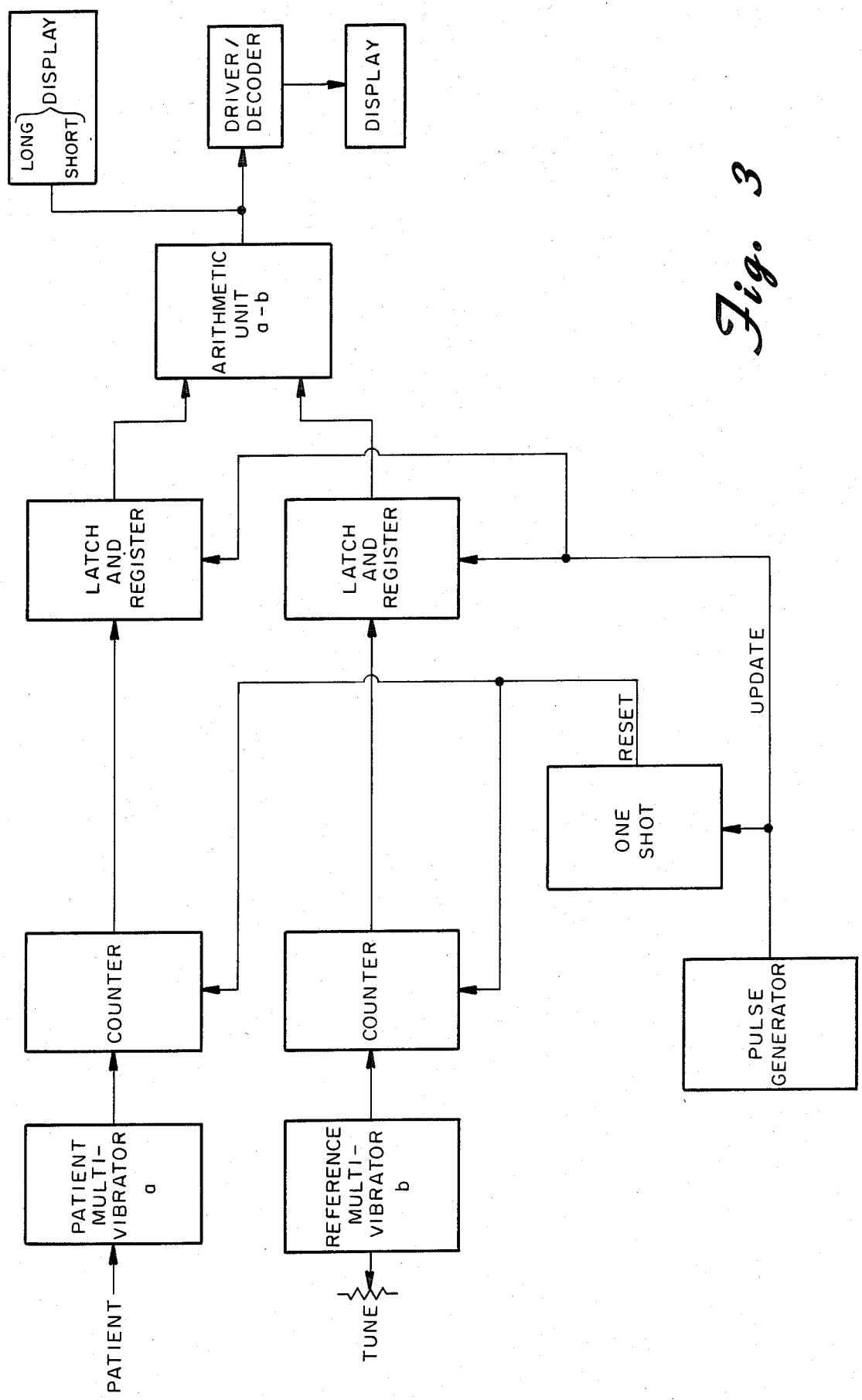
FIG. 3 is a block scheme of a second apparatus of the invention.

A second embodiment of the invention is illustrated in FIG. 3, wherein the order and attachment of the components is modified. This embodiment, a patient oscillator device, essentially identical to that described above, generates a wave form frequency dependent upon the impedance between the same two contacts. The oscillating wave signal is received by a counter, such as a BCD counter. The counter transmits the result to a register. When a pulse is received from the pulse generator in the update circuit, the number is transferred to the arithmetic unit, which is capable of performing an arithmetic function with that number and a number received at the same time from the parallel reference circuit. That reference circuit starts with a reference oscillator, essentially identical to that of the previous embodiment, capable of being tuned to the resistance or set to a value based upon the doctor's previous experience. The oscillating wave signal generated is passed through a counter, matched to that of the patient circuit. The count is, in turn, passed to a register which conveys the count when an update pulse is received, to the arithmetic unit. A reset circuit based upon a one-shot pulse generator is connected to the counters to begin the count over immediately after the update pulse is generated. The arithmetic function, preferably a differential between the two counts, is passed to a decode/driver circuit, which receives the signal and drives a numeric display. A second display device is connected to receive the arithmetic result from the arithmetic unit and signal whether the count for the patient is higher or lower than that of the reference circuit. This later display indicates whether the instrument is above or below the apical foramen.

While this invention has been described with reference to the specific embodiments disclosed herein, it is not confined to the details set forth and the patent is intended to include modifications and changes which may come within and extend from the following claims.

I claim:

1. An apparatus to determine the position of an instrument in a tooth and to display numerically the distance of the apical end of the instrument from the peridontal membrane around the tooth comprising, (a) a first electrical contact means to provide electrical connection from a circuit to an instrument for penetration into the tooth of a patient, (b) a second electrical contact means to provide electrical connection from the circuit electrically connecting to an electrical return to the patient, (c) a first oscillator means in the circuit electrically connected across the first and second contact means, to continuously generate an oscillating wave signal wherein the frequency of the wave signal is dependent upon the conductance between the first and second contact means, (d) a second oscillator means to continuously generate an oscillating wave signal as a reference signal set to a constant frequency, (e) an arithmetic frequency measuring and transmitting means to receive the signals from the first and second oscillator means, to determine an arithmetic relationship between the pulse rate of the signal from the first oscillator means and the pulse rate of the signal from the second oscillator means and transmit that arithmetic relationship, (f) at least one counter means to receive the arithmetic relationship and to determine the count of the value of the arithmetic relationship and transmit a coded signal of the relationship value of that count, (g) a decoder means to receive the coded signal and convert it to another signal to activate the appropriate sections of a numerical display means, (h) a register means to receive and hold the coded signal and convey a second coded signal upon receipt of an update interrupt signal, (i) an update means to cause removal of the information in the register means, after the duration of a pre-set period of time wherein the time period is chosen as directly proportional to a unit of distance of instrument travel in the tooth,
(j) a reset means to cause the counter means to reset to zero and resume counting again immediately after the interruption by the update means, and
(k) a numerical display means to receive the other signal and to display the arithmetic relationship.

2. The apparatus of claim 1 wherein a "divide by two" frequency means is connected in the circuit to receive the signals from the first oscillator means and the second oscillator means to divide the frequency by two and transmit the resulting signal to said counter means.

3. The apparatus of claim 1 wherein the arithmetic frequency measuring and transmitting means determines the subtractive differential between the frequencies of the first oscillator means and the second oscillator means.

4. The apparatus of claim 3 wherein a second display means is connected to receive the subtractive differential and arithmetic subtraction result from the arithmetic frequency measuring and transmitting means and display whether the frequency of the first oscillator means is higher than that of the second oscillator means or vice versa.

5. The apparatus of claim 1 wherein the second electrical contact means is capable of electrically connecting to a portion of the oral mucous membrane near the tooth to be treated.

6. The apparatus of claim 1 wherein an adjustment means is connected to the second oscillator means to set the constant frequency chosen by the operator based upon experience or upon a measurement of the conductance between the second contact means and a position on the peridontal membrane near the tooth to be treated.

7. An apparatus to determine the position of an instrument in a tooth and to display numerically the distance of the apical end of the instrument from the peridontal membrane around the tooth comprising,
(a) a first electrical contact means to provide electrical connection from a circuit to an instrument for penetration into the tooth of a patient,
(b) a second electrical contact means to provide electrical connection from the circuit to the patient,
(c) a first oscillator means in the circuit to continuously generate an oscillating wave signal electrically connected across the first and second contact means, wherein the frequency of the wave signal is dependent upon the conductance between the first and second contact means,
(d) a second oscillator means to continuously generate an oscillating wave signal as a reference signal set to a constant frequency,
(e) an arithmetic frequency measuring and transmitting means to receive the signals from the first and second oscillator means, to determine an arithmetic relationship between the pulse rate of the signal from the first oscillator means and the pulse rate of the signal from the second oscillator means, and transmit that arithmetic relationship in the form of a pulse,
(f) a counter means to receive the arithmetic relationship and to determine the count of the number of pulses and transmit a coded signal of that count,
(g) a decoder means to receive the coded signal convert it to another signal to activate the appropriate sections of a numerical display means,
(h) a register means to receive and hold the coded signal and convey a second coded signal upon receipt of an update interrupt signal,
(i) an update means to cause removal of the information in the register means, after the duration of a pre-set period of time wherein the time is chosen as directly proportional to a unit of distance of instrument travel in the tooth,
(j) a reset means to cause the counter means to resume counting again immediately after the interruption by the update means, and
(k) a numerical display means to receive the other signal to display the number of pulses 8. The apparatus of claim 7 wherein a "divide by two" frequency means is connected in the circuit to receive the signals from the first oscillator means and the second oscillator means to divide the frequency by two and transmit the resulting signal to said counter means.

9. The apparatus of claim 7 wherein the arithmetic frequency measuring and transmitting means determines the subtractive differential between the frequencies of the first oscillator means and the second oscillator means.

10. An apparatus to determine the position of the conductive apical end of an instrument in the root canal of a tooth with respect to the peridontal membrane around the tooth and display the distance numerically comprising,
(a) a first electrical contact means to provide electrical connection from a circuit to an instrument for penetration into the tooth of a patient,
(b) a second electrical contact means to provide electrical connection from the circuit to the patient,
(c) a first oscillator means in the circuit to continuously generate an oscillating wave signal electrically connected across the first and second contact means, wherein the frequency of the wave signal is dependent upon the conductance between the first and second contact means,
(d) a second oscillator means to continuously generate an oscillating wave signal as a reference signal set to a constant frequency,
(e) an arithmetic frequency measuring and transmitting means to receive the signals from the first and second oscillator means, to determine an arithmetic relationship between the pulse rate of the signal from the first oscillator means and the pulse rate of the signal from the second oscillator means and transmit that arithmetic relationship,
(f) a counter means to receive the arithmetic relationship and to determine the count of the value of the arithmetic relationship and transmit a coded signal of the relationship value of that count,
(g) a decoder means to receive the coded signal and convert it to another signal to activate the appropriate sections of a numerical display means,
(h) a register means to receive and hold the coded signal and convey a second coded signal upon receipt of an update interrupt signal,
(i) an update means to cause removal of the information in the register means, after the duration of a pre-set period of time wherein the time is chose as directly proportional to a unit of distance of instrument travel in the tooth and to transmit the update interrupt signal, (j) a reset means to cause the counter means to resume counting again immediately after the interruption by the update means, and (k) a numerical display means to receive the other signal and to display the arithmetic relationship.

11. An apparatus to determine the position of a conductive instrument in the root canal of a patient's tooth and to display numerically the distance of the apical end of the instrument from the apex of the root canal, comprising, (a) a first electrical contact means to provide electrical connection from a circuit to an instrument for penetration into the root canal, (b) a second electrical contact means to provide electrical connection from the circuit to the patient's body, (c) a first oscillator means in the circuit to continuously generate an oscillating wave signal electrically connected across the first and second contact means, wherein the frequency of the wave signal is dependent upon the conductance between the first and second contact means, (d) a second oscillator means to continuously generate an oscillating wave signal as a reference signal set to a constant frequency adjustable to a value dependent upon the conductance between the second contact means and the gigival sulcus of the patient, (e) a frequency differential measuring and transmitting means to receive the signals from the first and second oscillator means, to determine the difference between the pulse rate of the signal from the first oscillator means and the pulse rate of the signal from the second oscillator means and transmitting that difference, (f) a counter means to receive the difference and to determine the number of pulses and transmit that count to a numerical display means, (g) an update means to interrupt the pulse count of the counter means after the duration of a pre-set period of time chosen as directly proportional to a unit distance of the instrument travel in the tooth, (h) a reset means to cause the counter means to begin counting again immediately after the interruption by the update means, and (i) a digital display means to receive the count and to display the number of pulses.

* * * * *